United States Patent [19]

Lacey

[11] 4,389,877
[45] Jun. 28, 1983

[54] PIPING EROSION MONITORING SYSTEM

[76] Inventor: Walter J. Lacey, P.O. Box 59, Patterson, La. 70392

[21] Appl. No.: 248,552

[22] Filed: Mar. 27, 1981

[51] Int. Cl.³ .................. G01N 17/00; G01M 3/02
[52] U.S. Cl. ........................................ 73/37; 73/86; 116/268; 285/4
[58] Field of Search ............... 73/46, 86, 730, 37; 285/13; 116/268

[56] References Cited

U.S. PATENT DOCUMENTS

| 784,483 | 3/1905 | Erk | 73/46 |
|---|---|---|---|
| 2,756,076 | 7/1956 | Rodriguez, Jr. | 285/4 |
| 2,817,230 | 12/1957 | McCully | 73/46 |
| 3,794,057 | 2/1974 | Badger | 285/4 X |
| 3,846,795 | 11/1974 | Jones | 73/86 |
| 4,002,055 | 1/1977 | Kops | 73/40 |
| 4,002,059 | 1/1977 | Jeffers et al. | 73/86 |

FOREIGN PATENT DOCUMENTS 504638  4/1939  United Kingdom ............ 73/46

Primary Examiner—Daniel M. Yasich
Attorney, Agent, or Firm—David L. Ray

[57] ABSTRACT

A system to monitor the amount of erosion taking place within a pipe in which a point of reduced strength of the pipe is made by drilling a hole or notch to a preselected depth in a selected portion of the pipe wall. A hollow casing is provided around the point of reduced strength to provide a sealed zone. A conduit in the hollow casing is connected to a sensing device to monitor pressure changes when pipe failure occurs at the hole or notch.

10 Claims, 5 Drawing Figures

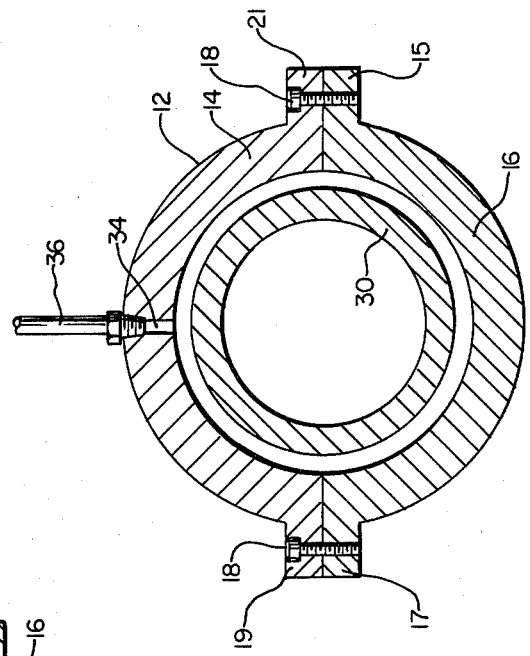
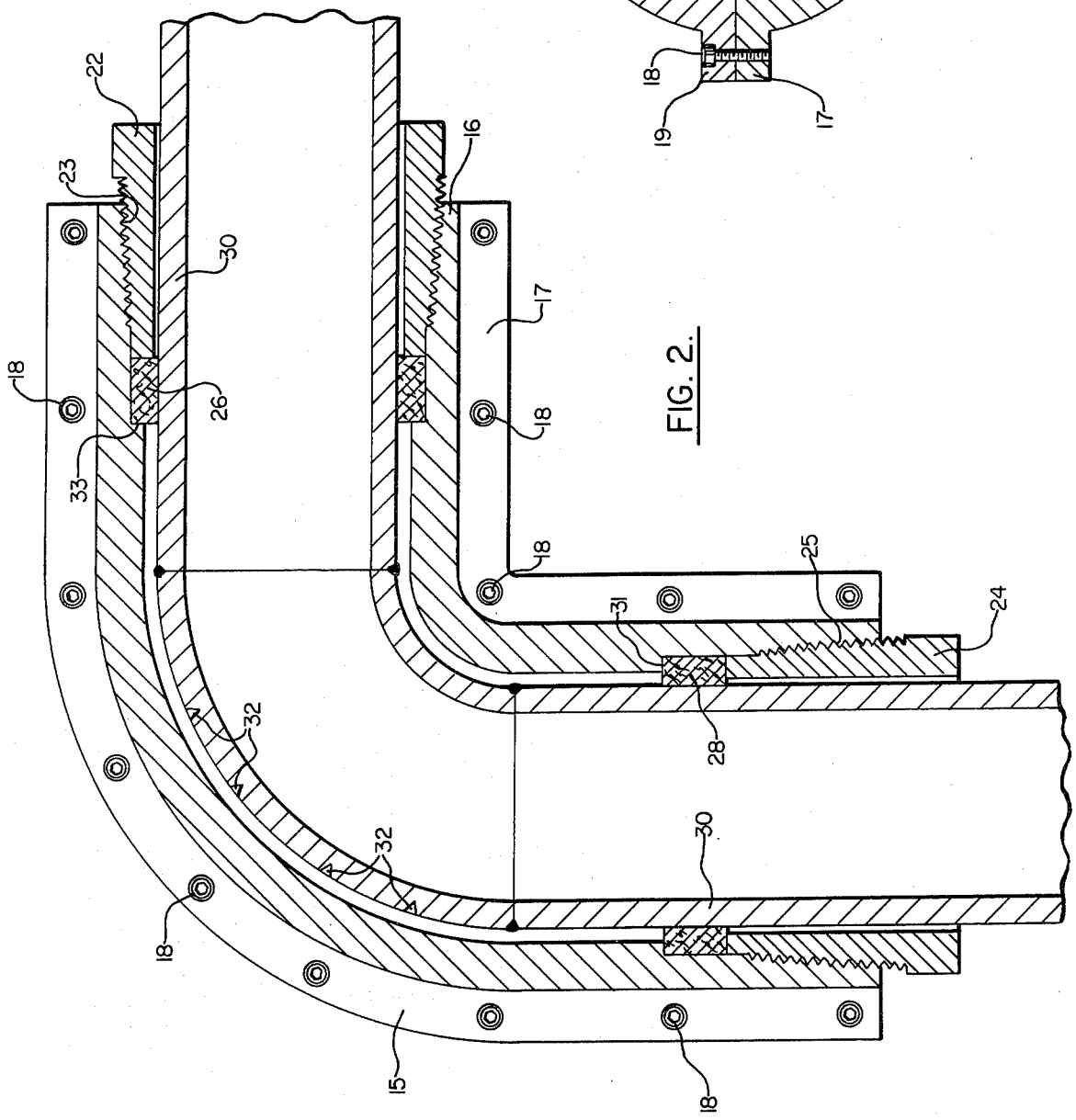

PIPING EROSION MONITORING SYSTEM

BACKGROUND OF THE INVENTION

Erosion of pipe walls has long plagued the chemical and oil and gas industries. In the chemical industries this erosion is usually due to the corrosive nature of the gas or liquids being carried in the pipes. In the oil and gas industry the erosion is most commonly mechanical in nature being caused by the impacting of solid materials carried by the flowing oil and gas as it passes through the pipes. These materials are most commonly sand which is brought to the surface by the hydrocarbons from the oil or gas reservoir which is being tapped. Pressures within the piping, whether the piping is being used in the chemical industry or in the oil and gas industry are often quite high. In the chemical industry such high pressures are the result of process pressures which are needed to accomplish the process being utilized. In the oil and gas industries the pressures are the result of the production from high pressure oil and gas reservoirs.

It can be appreciated that monitoring the amount of erosion taking place within the pipe is essential from both a safety aspect and a financial aspect. Should the erosion continue unmonitored there will be a point at which the piping wall becomes so thin that rupture of the piping will occur. Should any personnel be in the vicinity physical harm to these people is almost eminent. Also, from the financial aspect, rupture of piping can be catastrophic to adjacent equipment, not to mention the costly interruption of the chemical process or the gas and oil production being practiced at the time of failure. So well recognized is the necessity for monitoring the effects of erosion, several procedures have been developed which are nearly ubiquitous.

Two of the most widely utilized procedures provide intermittent monitoring. Generally a schedule is set up which invokes periodic checks, the length between checks being dependent upon the anticipated erosion rate. These two procedures are generally classified as radiographic inspection and ultrasonic inspection. The biggest drawback in utilizing these two procedures is their intermittent nature and do not provide continuous monitoring as would be the case in a passive monitoring system. This disadvantage is easily understood when it is considered, for example in the oil and gas industry, that the rate of erosion is not always constant. In producing oil and gas a producer attempts to achieve production without pulling sand from the reservoir along with the oil or gas product. However, this pulling of sand from the reservoir is not always preventable due to the uncertain nature of conditions found in the reservoir. Thus large amounts of sand may be flowing with the oil or gas product on an intermittent basis without the knowledge of the producer. As mentioned previously, this sand will cause erosion and since it can very well be on an intermittent basis the rate of erosion is not at all predictable. In the chemical industry intermittent erosion rates beyond that which is anticipated can also occur due to unit upset. Thus, when the inspection of the pipe walls is placed on a periodic basis there is always the possibility that erosion has occurred much faster than anticipated and that the inspections will not have the frequency required to warn of impending piping failure.

Not only is the very nature of radiographic and ultrasonic inspection, due to its periodic use, disadvantageous but the very procedures themselves are not without difficulty. In radiographic inspection, radioactive materials such as Iridium 192 or Cobalt 60 are utilized which always presents a hazard to the inspector and to any personnel around the inspection site. Also radiographic inspection is very time-consuming and as a result thereof is very costly. While ultrasonic inspection does not entail the use of radioactive material, it also has some drawbacks. For one, the surface of the pipe on which the inspection test is to be run must be prepared so that it is clean from rust, paint and other extraneous materials. If the rust buildup is quite heavy it will be necessary for the inspector to file the rust from the pipe which could be extremely dangerous if the pipe is near its bursting point. Also there will be a situation in which cleaning of the pipe may be nearly impossible due to the fact that the pipe is in an environment which makes cleaning an almost impossible task. For example, in off-shorer oil and gas operations the pipe to be tested may be located near the water line so that the wave action is continuously washing over the pipe making cleansing of the pipe for the purpose of ultrasonic inspection impossible. Ultrasonic inspectionn also suffers from the requirement that the device needs to be calibrated and such calibration is a time-consuming procedure.

Therefore there is a need for a system which will continuously monitor the wall thickness of pipe and will automatically notify the process operator or producer that the pipe wall has become dangerously thin. It is also desirable that such a system not require the use of hazardous, radioactive material or require time-consuming surface preparation or calibration.

THE INVENTION

This invention relates to a system for monitoring reduction in pipe wall thickness due to erosive or corrosive attack. The system includes providing at least one point of reduced strength in the piping adjacent the area anticipated to undergo the highest rate of reduction in wall thickness. A hollow casing is provided to encircle the pipe in a position to overlie the point of reduced strength. The casing has its inside walls spaced outwardly from the outside wall of the pipe at the point of reduced strength. A fluid seal is provided between the pipe and the casing so that there is provided a fluid seal zone which encompasses the point of reduced strength. An aperture is provided through the hollow casing which extends into the fluid sealed zone. This aperture is utilized for communicating fluid pressure changes in the zone to a sensory device which is in fluid pressure communication with the aperture. The point of reduced strength can be provided by simply forming a notch as by drilling a hole into the outside wall of the pipe to a depth whereby the remaining pipe wall thickness, before erosion or corrosion, at this point, is sufficient to contain expected fluid pressures. The depth of the hole will be determined for each situation based upon the material of construction of the pipe, the original wall thickness of the pipe, and the expected rate of reduction in wall thickness due to erosive or corrosive attack. Once the erosive or corrosive attack has reduced the wall thickness at the drilled hole, failure occurs solely at the hole and the pressurized fluid will escape into the fluid sealed zone. A sensory device will be in communication with this sealed zone and communication of the failure will be utilized to warn operating personnel or to actuate valves, etc., which may be utilized to shut down flow in the pipe.

As can be appreciated, the system of this invention is one which will continuously monitor the pipe and will give ample warning to the operating personnel that, when there is fluid escapement through the point of reduced strength, that the time has arrived to consider replacing the pipe in question. Also note that the leakage from the pipe into the fluid sealed zone does not result in total failure of the piping system as the leak is contained within the zone. Further, due to this containment there is no spillage of contaminating or polluting fluids in the area thereby protecting personnel from noxious substances and not requiring costly clean up.

As pointed out previously, if the conventional ultrasonic and radiographic inspections were utilized instead of the system of this invention, unexpected erosion or corrosion rates might result in pipe failure between periodic inspections. This failure could be catastrophic in nature, resulting in explosion as the failure would not be restricted to a small area but rather would most likely occur over a large portion of the pipe. Also the failure of the pipe would result in spillage of the fluid from the pipe.

These and other features contributing to satisfaction in use and economy in manufacture will be more fully understood when taken in connection with the following description of a preferred embodiment of this invention and the accompanying drawings in which identical numerals refer to identical parts and in which:

FIG. 2 is a sectional view through section lines 2—2 of FIG. 1;

FIG. 3 is a sectional view taken through section lines 3—3 of FIG. 1;

Figure 1:
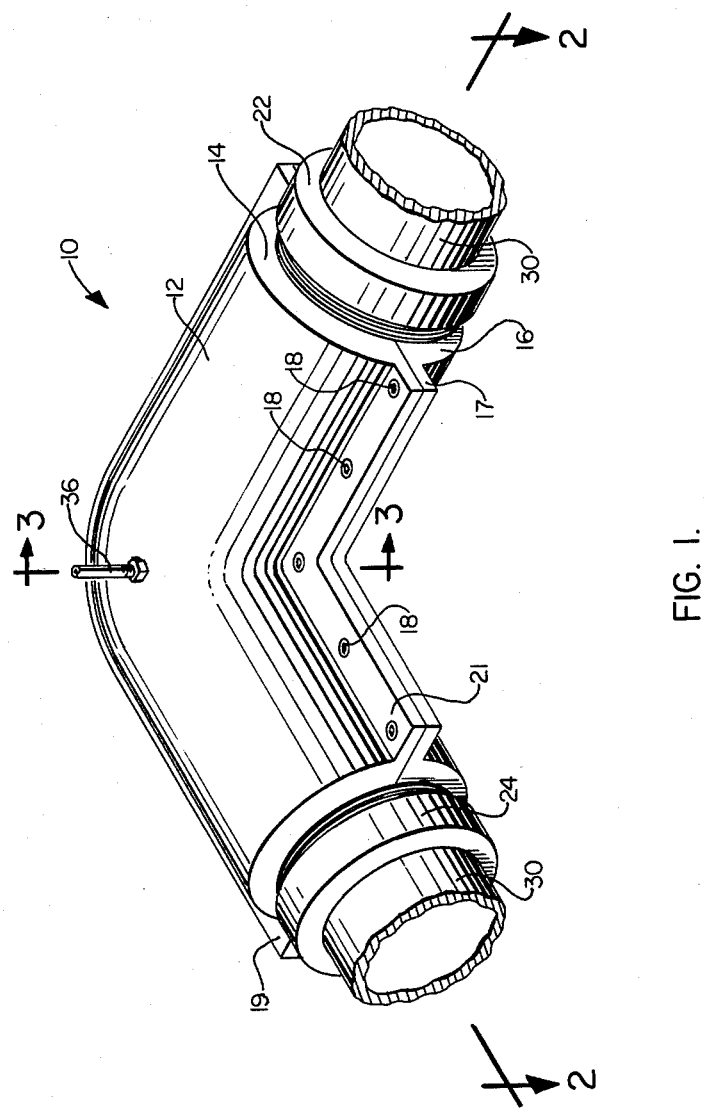
FIG. 1 is a perspective view of a system of this invention utilized on a piping elbow.

Referring now to FIGS. 1-3, there can be seen a system of this invention, generally designated by the numeral 10 for monitoring reduction in wall thickness of piping which reduction may be due to erosion or corrosion. Note that the embodiment shown in these figures is utilized on a piping elbow. It is to be understood that the system of this invention can be utilized on any type of piping configuration. A pipe elbow configuration was chosen for illustration as, generally speaking, the most severe erosion and corrosion will occur in the pipe elbow. Notice that the elbow shown in the drawings is a 90° elbow but it should be understood that elbows of other angularity may also present points of particularly high erosion or corrosion. It should also be pointed out that piping "T's" may also present erosion or corrosion points of trouble and that the system of this invention is easily adapted for fitment thereto with the principal of operation remaining the same and only the configuration of the system being changed to accommodate the piping configuration encountered.

As can be seen from FIGS. 1-3, system 10 includes a hollow casing, which is generally designated by the numeral 12. Hollow casing 12, for the embodiment shown in the drawings, is composed of two casing halves 14 and 16. These casing halves mate together by means of bolts 18 which are positioned around interior casing flanges 17 and 19 and exterior casing flanges 15 and 21. The mating of the casing halves along the flange lines is achieved in a manner so that a fluid-tight seal is produced along these flange lines. This can be easily accomplished by utilizing well-known sealing compounds or by the utilization of gaskets, the material used to achieve the fluid seal being only dependent upon the pressures anticipated and upon the corrosive nature of the product expected in the pipe line. Determination of the particular sealing material to be utilized will be well within the knowledge of one skilled in the art as such sealing must be accomplished in other places in the process stream.

Note that casing 12 encircles and overlies the elbow portion of the pipe line 30. This is necessary as it is expected that the greatest amount of erosion or corrosion will take place in the elbow portion of the piping line. Also note that there is an annular space between the outside wall of piping line 30 and the inside wall of casing 12. As will be hereinafter described, this annular space will form part of a fluid sealed zone.

To provide a fluid-tight seal at the ends of casing 12 there is provided a seal at each casing end, as can be seen in FIGS. 1 and 2. FIG. 2 shows that each seal has an annular ring of sealing material labeled 28 and 26 and a threaded sealing collar labeled 22 and 24. To help hold annular sealing material 28 and 26 there is provided an annular recess at the distal end of each of the internal threads which are cut into the casing ends. These annular recesses are labeled 31 and 33 in FIG. 2. Collars 24 and 22 achieve threaded cooperation with the internal casing threads and this threaded cooperation is designated 23 and 25 in FIG. 2. It can be appreciated as collars 24 and 22 are tightened they will press and deform annular sealing material 28 and 26 respectively so that a fluid-tight seal is achieved between the inside wall of casing 12 and the exterior wall of piping 30. A choice of material for annular seals 28 and 26 is dependent upon pressures anticipated and also the corrosive nature of the material to be found in piping 30.

In FIG. 2 it is seen that there are provided points of reduced strength 32 in the outside wall of piping 30. Since, as before said, the most amount of erosion or corrosion will be taking place in the elbow portion of piping 30, placement of points 32 is most advisably made in that area of anticipated stress. The depth and size will be dependent upon the wall thickness at which the user of the pipe line considers critical. In other words, if the user of the pipe line feels that he can tolerate a thin wall thickness, then the depth of points 32 will be not as great as would be the case of another pipe line user who would wish to keep his pipe line at a greater wall thickness.

Figure 5:
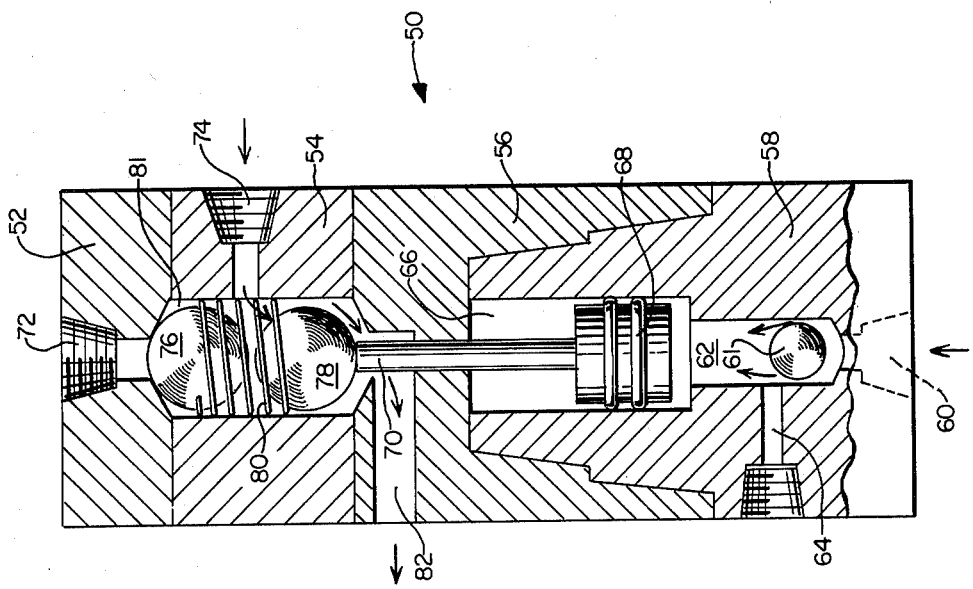
FIG. 5 is a sectional view of the sensory device shown in FIG. 4 in a different operating mode.
Figure 4:
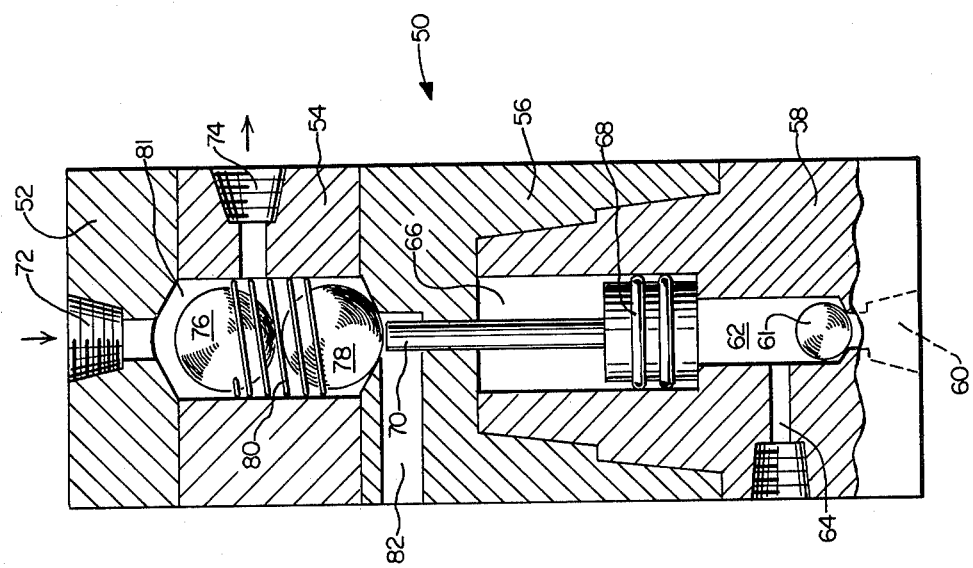
FIG. 4 is a sectional view taken through a sensory device utilized with the system shown in FIG. 1.

In communication with the fluid-sealed zone there is provided aperture 34 through casing 12. As shown in FIG. 3, there is attached to aperture 34 fluid conduit 36. Fluid conduit 36 is in communication with a sensory device such as the one shown in FIGS. 4 and 5. The sensory device shown in FIGS. 4 and 5 can be utilized to operate a cut-off valve which would turn off fluid flow in pipe 30. Since the sensory device 50 shown in FIGS. 4 and 5 is connected to the fluid-sealed zone by means of the before-described conduit 36, conduit 36 is attached, by appropriate coupling means, to sensory device 50 at fluid input port 60. Device 50 provides a lower and upper manifold which will hereinafter be described. Various channels, cylinders, etc., in device 50 are easily made up by the utilization of blocks 52, 54, 56 and 58 which are individually machined and then fitted together by means of conventional bolting techniques. One of the aforementioned manifolds, i.e., the lower manifold, comprises a fluid input port 60, chamber 62, fluid dump port 64 and cylinder 66. To selectively close off fluid input port 60 there is provided check valve 61. Within cylinder 66 is piston 68. When pressure from the fluid-sealed zone is received through conduit 36 to fluid input port 60, check valve 61 is moved from sealing engagement and chamber 62 is pressurized. Fluid dump port 64 is closed off at this time. Pressurized fluid in chamber 62 is communicated to the base of piston 68 so that it moves upward within cylinder 66. Push rod 70 which passes from the lower manifold to the upper manifold moves upward along with piston 68.

The other aforementioned manifold, i.e., the upper manifold, includes an instrument gas input port 72, an instrument gas outlet 74 and an instrument gas dump port 82. Chamber 81 is in communication with all three of these ports. Within chamber 81 is a valving system comprising balls 76, 78 and spring 80. When the valving system is undisturbed, i.e., push rod 70 is in the retracted position, instrument gas input port 72 opens. Thus instrument gas 72, which in most cases will be a gas under positive pressure, will be utilized, for example, to maintain a valve in the open position. Of course, the instrument gas may be utilized to operate warning devices such as sirens, bells, etc. It is also to be understood that instead of utilizing a positive pressure through instrument gas that a vacuum may also be utilized. When a vacuum is utilized closure of instrument gas input port 72 will result in failure of the vacuum in the line hooked to instrument gas outlet port 74 thereby activating whatever instrumentality is attached thereto. Assuming, however, that positive pressured instrument gas is utilized, and that piston 68 has been forced upward by receipt of a fluid under positive pressure from the fluid-sealed zone, the following scenario is followed by sensory device 50. Since piston 68 is moved upward push rod 70 likewise moves upward, as is shown in FIG. 5, thereby accomplishing two valving steps. As push rod 70 moves upward it displaces ball 78 from its sealed position cutting off instrument gas. The positive pressurized instrument gas which is in the line connected to instrument gas outlet port 74 is then free to follow a path so that it is dumped to the atmosphere through instrument gas dump port 82 as shown in FIG. 5. Loss of pressure will actuate the valve, alarm or whatever is connected to instrument gas outlet port 74. After the alarm or valving function has been accomplished and the operator has taken whatever action he desires, placement of sensory device 50 in the mode shown in FIG. 4 is accomplished by opening of the valve attached to fluid outlet port 64 so that the pressurized fluid can be released and piston 68 can return to its original position. Also ball 78 will move to make the seal shown in FIG. 4 and ball 76 will move from its sealing position at instrument gas inlet port 72.

While the sensory device shown in FIGS. 4 and 5 is especially suitable for use in the system of this invention, it should also be realized that other sensory devices may be utilized, the only requirement being that the sensory device be actuated in response to the build up of pressure in the fluid-sealed zone as a result of failure of any one of the points of reduced strength in the piping line which is encased by the casing.

All materials of construction should be such that they are capable of withstanding the pressures anticipated and also able to withstand any corrosive environment which they may encounter.

What is claimed is:

1. A system for monitoring reduction in wall thickness in piping due to erosion or corrosion, which system comprises:
    a. at least one point of reduced strength in said pipe in the area anticipated to undergo the highest rate of reduction in wall thickness;
    b. hollow casing means encircling at least a portion of said pipe and positioned to overlie and encompass said point, said hollow casing means having its inside wall spaced outwardly from the outside pipe wall at least at said point;
    c. sealing means for achieving a fluid seal between said pipe casing, said sealing means providing a fluid seal zone encompassing said point; and
    d. an aperture through said hollow casing extending to said zone and having conduit means attached thereto for communicating fluid pressure changes in said zone to a sensory means in fluid pressure communication with said aperture, wherein said point of reduced strength is a notch formed into the outside wall of said pipe to a preselected depth whereby the remaining pipe wall thickness at the site of said notch is sufficient to contain the fluid pressure in said pipe until a predetermined amount of said pipe wall at said notch has been reduced in thickness by erosion or corrosion.

2. The system of claim 1 wherein said hollow casing means comprises,
    i. a pair of casing halves which are mateable along a plane parallel to their center axis, and
    ii. mating means to achieve a fluid sealed mating of said halves.

3. The system of claim 1 wherein said hollow casing is tubular and has an inside diameter larger than the outside diameter of said pipe.

4. The system of claim 1 wherein said pipe includes a pipe elbow which is connected at both of its ends to a length of linear pipe and said hollow casing means encloses all of said pipe elbow and at least a portion of said linear pipe lengths.

5. The system of claim 1 wherein said hollow casing means is internally threaded at both of its ends and has an annular recess at the distal end of each of said internal threads and said sealing means comprises, for each end of said hollow casing means,
    i. a threaded collar for threading into said internally threaded ends of said hollow casing means, and
    ii. a ring of sealing material fittable in said recess which will deform and press against the inside wall of said casing means and the outside wall of said pipe upon tightening of said threaded collar.

6. The system of claim 5 wherein said casing means is tubular and has an inside diameter larger than the outside diameter of said pipe.

7. The system of claim 5 wherein said hollow casing means comprises,
    i. a pair of casing halves which are mateable on a plane parallel to their center axis, and
    ii. mating means to achieve a fluid sealed mating of said halves.

8. The system of claim 1 wherein said sensory means is in fluid pressure communication with said aperture by means of a conduit connected at one of its ends to said aperture and the other of its ends to said sensory means.

9. The system of claim 8 wherein said sensory means comprises a first and second manifold, said first manifold having a fluid input port, a check valve for opening and closing said fluid input port in response to positive fluid pressure change, a cylinder in fluid communication with said fluid input port, a piston fittable within said cylinder, and a push rod attached to said piston, said push rod extending through said first manifold into a second manifold; and said second manifold having an instrument gas input port, an instrument gas outlet port in communication with said instrument gas input port, a gas dumping port in communication with said instrument gas output port, and valving means within said second manifold and in contact with said push rod to selectively place, in response to movement of said push rod, either said instrument gas input port or said instrument gas dumping port in gas communication with said instrument gas outlet port.

10. The system of claim 9 wherein said sensory means additionally has a fluid dumping port in said first manifold in fluid communication with said fluid input port and said cylinder.

* * * * *